United States Patent
Waksmundzki et al.

(10) Patent No.: US 6,575,949 B1
(45) Date of Patent: Jun. 10, 2003

(54) PERFORATED STRETCH EAR DIAPER

(75) Inventors: Andrew Waksmundzki, Jackson, NJ (US); Lanying Wu, Devon, PA (US); Joan Rodgers, Brookhaven, PA (US)

(73) Assignee: Tyco Healthcare Retail Services AG (CH)

( * ) Notice: Subject to any disclaimer, the term of this patent is extended or adjusted under 35 U.S.C. 154(b) by 0 days.

(21) Appl. No.: 10/091,014

(22) Filed: Mar. 5, 2002

(51) Int. Cl.⁷ ................................................ A61F 13/15
(52) U.S. Cl. ................... 604/385.11; 604/389; 604/391
(58) Field of Search .................... 604/389, 391, 604/385.01, 385.11, 385.22, 385.23, 385.24

(56) References Cited

U.S. PATENT DOCUMENTS

| | | | |
|---|---|---|---|
| 3,800,796 A | | 4/1974 | Jacob |
| 4,014,338 A | | 3/1977 | Schaar |
| 4,036,233 A | | 7/1977 | Kozak |
| 4,066,081 A | | 1/1978 | Schaar |
| 4,074,716 A | | 2/1978 | Schaar |
| 4,090,516 A | | 5/1978 | Schaar |
| 4,158,363 A | | 6/1979 | Schaar |
| 4,209,016 A | | 6/1980 | Schaar |
| 4,389,212 A | | 6/1983 | Tritsch |
| 4,515,595 A | | 5/1985 | Kievit et al. |
| 4,619,649 A | | 10/1986 | Roberts |
| 4,735,622 A | | 4/1988 | Acuff et al. |
| 4,826,499 A | | 5/1989 | Ahr |
| 5,137,525 A | * | 8/1992 | Glassman ............... 604/385.11 |
| 5,236,430 A | | 8/1993 | Bridges |
| 5,242,436 A | * | 9/1993 | Weil et al. ............. 604/385.29 |
| 5,246,433 A | * | 9/1993 | Hasse et al. ................. 604/396 |
| 5,496,298 A | | 3/1996 | Kuepper et al. |
| 5,618,280 A | * | 4/1997 | Glackin et al. ......... 604/385.08 |
| 5,624,420 A | | 4/1997 | Bridges et al. |
| 6,022,430 A | | 2/2000 | Blenke et al. |
| 6,049,023 A | * | 4/2000 | Blenke et al. ............... 604/365 |
| 6,120,489 A | | 9/2000 | Johnson et al. |
| 6,316,687 B1 | * | 11/2001 | Davis et al. ................. 604/372 |
| 6,450,996 B1 | * | 9/2002 | Otsubo ................... 604/385.01 |
| 6,508,797 B1 | * | 1/2003 | Pozniak et al. ......... 604/385.11 |
| 2002/0032427 A1 | * | 3/2002 | Schmitz et al. ......... 604/385.11 |

* cited by examiner

*Primary Examiner*—Weilun Lo
*Assistant Examiner*—Michael Bogart
(74) *Attorney, Agent, or Firm*—Caesar, Rivise, Bernstein, Cohen & Pokotilow, Ltd.

(57) ABSTRACT

A diaper is provided which includes a chassis having front, rear, and crotch portions. The chassis includes a topsheet, backsheet, core and pair of ears. Each ear includes a topsheet, backsheet and proximal, distal, first connecting, and second connecting edges. The first connecting and second connecting edges connect the distal to proximal edges. The proximal edge is integral to the chassis. Each ear has an elastic layer sandwiched between its topsheet and backsheet. Each elastic layer has first and second edges which are secured to the ear topsheet and backsheet. The elastic layer has a central portion not secured to either the ear topsheet or backsheet. Each ear topsheet and backsheet has perforations. The tearable portion is adjacent to the central portion. Each ear may be pulled away from the chassis causing the ear topsheet and backsheet to tear at the perforations thereby exposing the elastic layer.

16 Claims, 1 Drawing Sheet

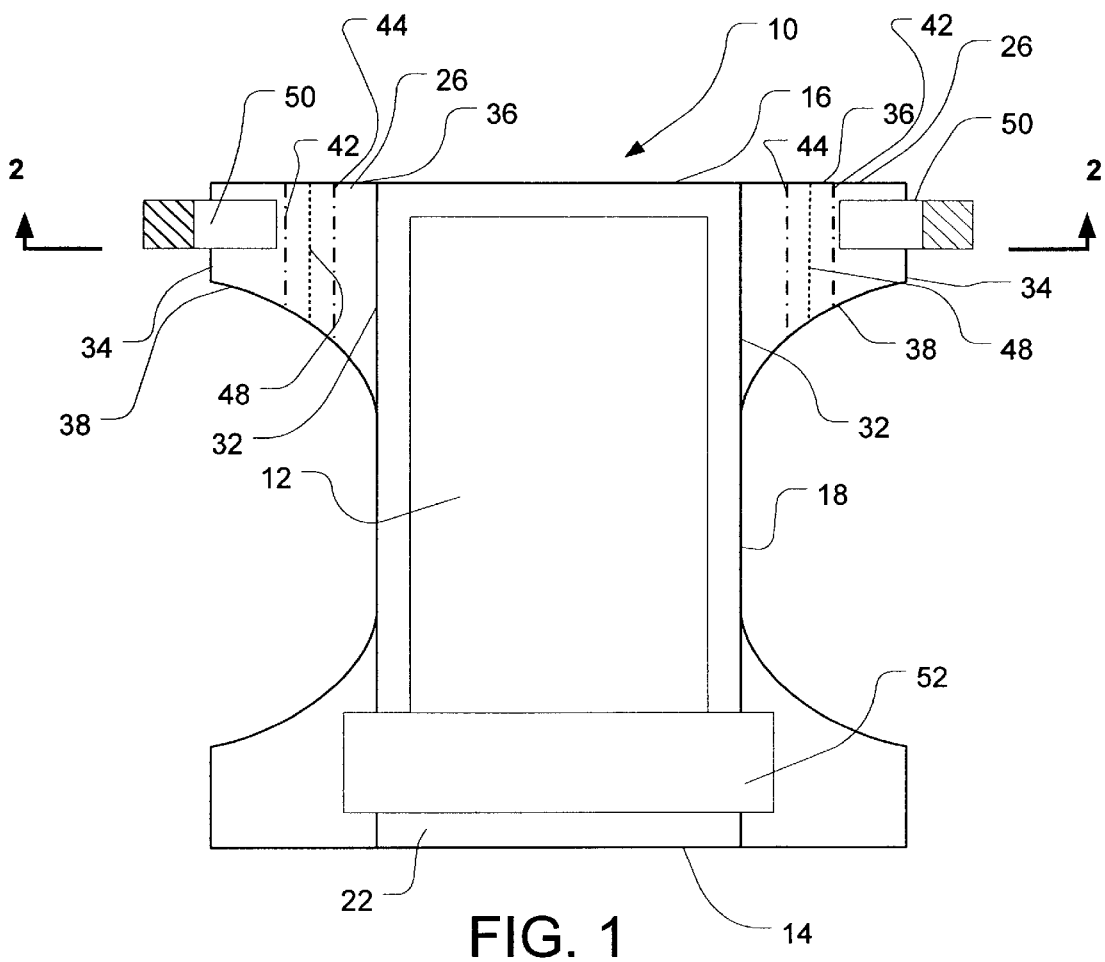
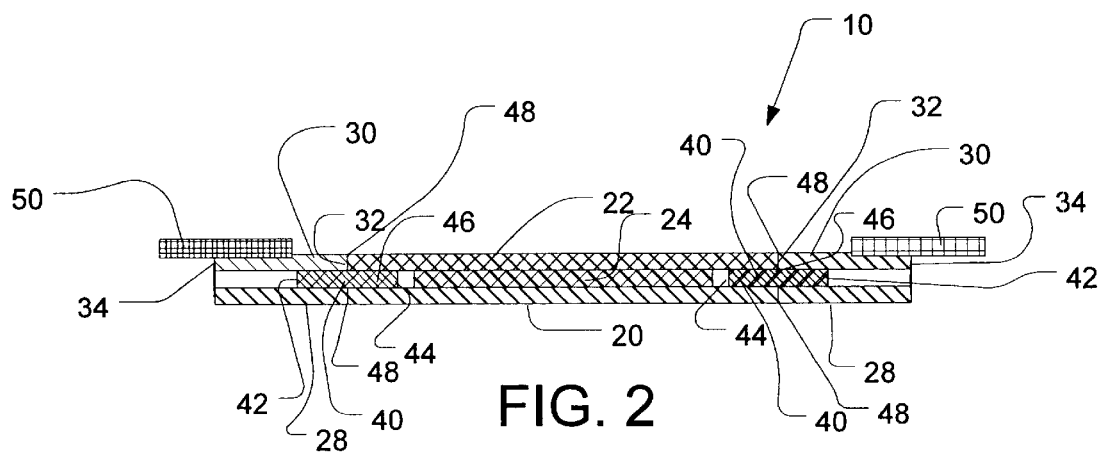

PERFORATED STRETCH EAR DIAPER

FIELD OF INVENTION

This invention relates to disposable absorbent articles. Specifically, the present invention relates to ears on disposable absorbent articles, such as diapers, that utilize an elastomeric feature.

Disposable absorbent articles such as disposable diapers, training pants, adult incontinence garments, and the like are known. In the past, particularly in the case of infant diapers, such absorbent articles were generally formed with an hourglass configuration. The narrower portion of the article was adapted to be placed between the legs of the wearer with the wider portions of the article being adapted to encircle the waist of a wearer so that the front and rear portions overlapped and could be easily attached to one another. Recently, it has become desirable to produce absorbent articles, such as infant diapers, which fit more closely to the body of a wearer. Accordingly, it has become desirable to make such articles smaller and less conspicuous in use while still maintaining a high level of absorbent protection.

Specifically, it has become desirable to produce disposable absorbent articles which have a relatively narrow crotch section and a narrower overall width when compared to typical disposable absorbent articles. Leg openings are defined, in part, on traditional infant diapers by the overlapped front and rear portions of the diaper. Such leg openings are generally perceived as providing good absorbent protection. If the front and rear portions of the diaper do not completely encircle the waist of a wearer and overlap with one another, there is a perception of decreased leakage performance.

Known fastening devices for absorbent articles which do not completely encircle the waist of a wearer have generally consisted of relatively narrow rectangular means or beltlike means to hold the article in place around the waist of a wearer. Such known means do not generally correct for the perceived decrease in absorbent performance. Further, known means of fastening such articles about the waist of a wearer can lead to undesirable red marking of the skin of a wearer.

The major function of absorbent garments such as disposable diapers is to absorb and contain body exudates. Such articles are thus intended to prevent body exudates from soiling, wetting, or otherwise contaminating clothing or other articles, such as bedding, that come in contact with the wearer. In general, disposable diapers all have the same basic structure which comprises a liquid permeable topsheet, a liquid impermeable backsheet, an absorbent core positioned between the topsheet and said backsheet, and a means for fastening the diaper about the wearer's waist.

The prior art teaches numerous variations of fastening systems. In order to try to improve the fit of the diaper, a number of ways have been attempted to provide elastic fastening systems in the diaper. For example, U.S. Pat. No. 3,800,796 (Jacob) teaches an elastic strip fastener tab which provides as diaper with an elastically extensible side waistband. Other techniques for providing elastic characteristics in tape tabs are disclosed in U.S. Pat. No. 4,209,016, (Schaar); U.S. Pat. No. 4,158,363 (Schaar); U.S. Pat. No. 4,090,516 (Schaar); U.S. Pat. No. 4,074,716 (Schaar); U.S. Pat. No. 4,006,081 (Schaar); and U.S. Pat. No. 4,389,212 (Tritsch). A technique for providing a diaper with a stretchable waistband so as to improve fit is disclosed in U.S. Pat. No. 4,036,233 (Kozak) and which teaches a diaper fabricated from a stretchable material which is bonded to a non-stretchable material, wherein openings are provided in the waistband area of the non-stretchable material to permit stretching of the stretchable material. Fastening tapes are then attached to the stretchable waistband. Still another technique for providing a diaper with a stretchable waistband so as to improve fit is disclosed in U.S. Pat. No. 4,014,338 (Schaar) and which teaches a pleated diaper having an elastic member in a waistline portion thereof, to which fastening means are attached.

Typical elastic fastening systems include a full stretch ear. A full stretch ear is expensive in materials and processes to construct. Alternatively, a stretchable tape is used. However, the stretchable tape offers limited stretch in the location of the ear.

Other prior art include the following. U.S. Pat. No. 4,619,649 (Roberts) discloses a disposable toddler training panty having a thin plastic outer layer and an elastic waistband and leg bands. Perforations extend down the sides of the panty to accommodate removal of the panty once used.

U.S. Pat. No. 4,735,622 (Acuff, et al.) discloses a disposable training panty having an elastic waistband and elastic legs. Perforation lines extend down the side of the panty to accommodate removal.

U.S. Pat. No. 4,826,499 (Ahr) discloses a disposable absorbent garment such as a disposable diaper which includes a fastening system that comprises laterally displaceable elastic members affixed to the chassis of the diaper. The fastening means, rather than being affixed to the garment in a fixed relation, are laterally displaceable in relation to the balance of the garment. That is, the fastening means is capable of moving in a direction parallel to the lateral center line of the diaper when the diaper is in its flat out, uncontracted state, as shown in FIG. 1 of this patent. The remaining part of the diaper, the chassis, remains fixed.

U.S. Pat. No. 5,496,298 (Kuepper et al.) discloses elastomeric ears for disposable absorbent articles. No perforations or similar separatable means are disclosed.

U.S. Pat. No. 5,624,420 (Bridges et al.) discloses portable training pants having a non-perforated tear line through the elastic. This tear line is for removal of the training pants.

While the fastening systems discussed above do provide some measure of improvement over non-elastic fastening systems, the devices fail to adequately address the need for a cost-effective fastening system which provides the garment with a better fit, improved adjustability and substantial stretch in the area of the ear.

All references cited herein are incorporated herein by reference in their entireties.

BRIEF SUMMARY OF THE INVENTION

A disposable absorbent article that is arranged to be worn by a living being to trap and collect loose waste of the being is provided. The absorbent article includes a main chassis configured to be worn between the legs of the being. The chassis has a front portion, a rear portion and a crotch portion connecting the front portion and the rear portion. The chassis includes a liquid permeable chassis topsheet and a liquid impermeable chassis backsheet. The topsheet is directed toward the being's skin. The chassis also includes an absorbent core positioned between the chassis topsheet and the chassis backsheet and a pair of ears integral to the rear portion of the chassis. Each ear includes an ear topsheet and an ear backsheet. Each ear has a proximal edge, a distal edge, a first connecting edge and a second connecting edge.

The first connecting edge and the second connecting edge connect the distal to the proximal edge. The proximal edge of each ear topsheet and backsheet is integral to the topsheet and backsheet of the chassis. Each ear has an elastic layer sandwiched between at least a portion of the ear topsheet and the ear backsheet. Each elastic layer has a first edge and a second edge. The first edge is secured to the ear topsheet and the ear backsheet and the second edge is secured to the ear topsheet and the ear backsheet. The elastic layer has a central portion not secured to either the ear topsheet or the ear backsheet. Each ear topsheet and each ear backsheet has a tearable portion extending from the first connecting edge to the second connecting edge. The tearable portion extends along the central portion of the elastic layer. A fastener joined to each of the ears secures the disposable absorbent article about a wearer's waist. A portion of each ear may be pulled away from the chassis causing the ear topsheet and the ear backsheet to tear at the tearable portion thereby exposing the central portion of the elastic layer.

In a preferred embodiment, the disposable absorbent article is a diaper. Preferably, the tearable portion on each ear topsheet overlaps the tearable portion on each ear backsheet. The tearable portion extending from the first connecting edge to the second connecting edge may be at a point adjacent the main chassis. Alternatively, the tearable portion may be at a point adjacent the distal edge. The fasteners may include fastening tape extending between the ear backsheet of each of the ears and a landing zone on the backsheet which is arranged to receive the tape. The fastening tape may be adhesive tape or otherwise include use of an adhesive. The elastic material may extend substantially from the proximal edge to the distal edge, and from the first connecting edge to the second connecting edge.

The tearable portion may include a plurality of perforations and preferably includes a series of spaced perforations in a generally straight line. Preferably, the topsheet is liquid permeable and the backsheet is liquid impermeable.

BRIEF DESCRIPTION OF SEVERAL VIEWS OF THE DRAWINGS

The invention will be described in conjunction with the following drawings in which like reference numerals designate like elements and wherein:

FIG. 1 is top, plan view of a disposable absorbent article in accordance with one preferred embodiment of the present invention; and FIG. 2 is a partial, simplified, cross sectional view of the disposable absorbent article of FIG. 1 taken substantially along lines 2—2 of FIG. 1.

DETAILED DESCRIPTION OF THE INVENTION

Referring now to the drawings, wherein like part numbers refer to like elements throughout the several views, there is shown in FIGS. 1 and 2, a disposable absorbent article 10 in accordance with one preferred embodiment of the present invention. It should be pointed out that, as used herein, the term "disposable" means that the article is designed to be used until soiled, either by urination or otherwise, and then discarded, rather than being washed and used again.

In the embodiment of FIGS. 1 and 2, the disposable absorbent article 10 is in the form of a diaper. While the following description focuses on diapers, it should be clear that the subject invention can be used for any type of absorbent article or garment to be worn by a person for trapping urine or menses.

The disposable absorbent article 10 includes a main chassis 12 having a front portion 14, a rear portion 16, and a crotch portion 18 connecting the front portion 12 and the rear portion 16 and may be of generally conventional construction, except for its stretchable ear construction, as will be described below, for improved securability of the absorbent article 10 at low cost. As best seen in FIG. 2, the chassis 12 further includes a liquid permeable topsheet 20, a liquid impermeable backsheet 22, an absorbent core 24 positioned between the chassis topsheet 20 and the chassis backsheet 22, and a pair of ears 26 integral to the rear portion 16 of the chassis 12.

The topsheet 20 is arranged to face toward the body of the user, i.e., against the skin of the wearer, when the disposable absorbent article 10 is in place, with the backsheet 22 facing away from the wearer. The topsheet 20 is superimposed over the backsheet 22, with the absorbent core 24 interposed therebetween. The topsheet 20 and/or backsheet 22 can be any suitable shape and dimensions for a design of a disposable absorbent article 10.

The topsheet 20 may be of the same shape as the backsheet 22 or of a different shape, and is bonded to the backsheet 22 at least around the periphery of the absorbent core. The absorbent core 24 is interposed between the topsheet 20 and the backsheet 22. The backsheet 22 and topsheet 20 can be joined together in any suitable manner, e.g., by adhesive bonding. The adhesives can be applied in any manner such as spraying, slot-coat extrusion, printing, or the like. The applied adhesive can be in any desired configuration or design, such as continuous or discontinuous beads, continuous or discontinuous swirls, meltblown patterns, spray patterns or the like. Alternatively, the joining of layers and structure can be accomplished by heat sealing, ultrasonic bonding, or the like.

Each ear 26 includes an ear topsheet 28 and an ear backsheet 30. Each ear 26 further has a proximal edge 32, a distal edge 34, a first connecting edge 36 and a second connecting edge 38. The first connecting edge 36 and the second connecting edge 38 connect the distal edge 34 to the proximal edge 38. The proximal edge 38 of each of the ears is integral to the chassis 12. Like the main chassis 12, the ear topsheet 28 and the ear backsheet 30 may be bonded around their periphery, e.g. along the proximal edge 32, distal edge 34, first connecting edge 36 and second connecting edge 36.

As can best be seen in FIG. 2, each ear 26 has an elastic layer 40 sandwiched between the ear topsheet 28 and the ear backsheet 30, or a portion thereof. Each elastic layer 40 has a first edge 42 and a second edge 44. The first edge 42 of the elastic layer 40 is secured to the ear topsheet 28 and the ear backsheet 30 and the second edge 44 is secured to the ear topsheet 28 and the ear backsheet 30. The elastic layer 40 has a central portion 46 that is not secured to either the ear topsheet 28 or the ear backsheet 30.

Securement of the elastic layer 40 to the topsheet 20, backsheet 22, ear topsheet 28 and ear backsheet 30 may be accomplished along the first edge 42 and the second edge by, for example, a construction adhesive or by ultrasound or thermal-mechanical means.

The elastic layer 40 may be a fluted elastic or stretch non-woven laminate material obtained, for example, from Tredegar Films of Richmond, Va.

Each ear topsheet 28 and each ear backsheet 30 have a tearable portion 48 extending from the first connecting edge 36 to the second connecting edge 38. The tearable portions 48 are adjacent to the central portion 46 of the elastic layer 40. The tearable portions 48 are preferably in the form of a plurality of perforations extending in a substantially straight line (or a curved line) from the first connecting edge 36 to the second connecting edge 38. The perforations may be in the form of continuous slits that are separated be small areas of material. The small areas of material may comprise of only one or more fibers of material. When tightening the article 10 around the waist of a user, the ears 26 are pulled from a point adjacent the distal edges 34 of the ears 26 such that the tearable portions (perforations) 48 separate thereby exposing the elastic layer 40 to allow stretch of the a portion of the ear with respect to the chassis 12. The width of elastic layer 40, i.e., how far it extends between the distal end 34 and proximal end 36 of the ears 26, determines the availability of stretch. This feature will be described in more detail below.

A fastener, such as a length of adhesive backed tape 50, is joined to the ear backsheet 30 of each of the ears 26 to secure the disposable absorbent article 10 about a wearer's waist.

The backsheet 22 and ear backsheet 30 are preferably formed from a laminated sheet of a non-woven material and film (with the non-woven side positioned as the outermost layer). Such material should be hydrophobic, soft in texture, and strong in tensile strength. One particularly suitable material is a spunbond-meltblow-spunbond (SMS) web having a basis weight of about 10 to 20 gms per square meter (gsm), available from AVGOL Nonwoven Industries LTD., Holon, Israel. The spunbond layer is made of polypropylene fibers. Such composites provide the dual advantages of liquid barrier properties of film along with a soft, warm outer fabric texture. The non-woven outer cover can also be made of other suitable cloth-like materials, e.g., spun-bond or thermal-bond non-woven web made of either polypropylene, polyethylene, polyester, bi-component fibers (polyethylene/polypropylene or polyethylene/polyester), or any combinations of these fibers. Various multiple layer configurations or fiber denier variations may be used. Another example includes hydro-entangled non-woven webs, which may contain some cotton and/or rayon fibers blending in with thermal-plastic fibers. Cellulose fibers can also be blended in at small percentages to reduce cost. Still another example is a non-woven outer-cover made of stretchable or elastic materials, such as elastomeric composites of non-woven(s) and elastic membranes or a single layer of elastic material. The elastomeric composite can comprise an inner layer of pre-stretched extruded elastic film sandwiched between and attached to a pair of non-woven webs. The non-woven webs may consist of spun-bond web, thermal-bond web, or a combination of the two. Preferably, the elastic film is made of synthetic rubber and the non-woven made of spun-bond polypropylene.

Other materials for forming the backsheet 22 and ear backsheet 30 may include polypropylene films, co-extruded films (polyethylene and ethylene vinyl acetate), co-polymer films (polyethylene/polypropylene), and polylaminates (polypropylene nonwoven and polyethylene film). Still another example is a film made of a "breathable' microporous polyethylene. Suitable breathable films are available from Exxon Chemical Company, Buffalo Grove, Ill. This material allows water vapor to pass through it over time, while being impervious to liquid water. The water vapor transmission rate may range from 200–2000 grams per square meter per 24-hour period.

In order to enable urine to quickly and efficiently pass through the topsheet 20 and into the absorbent core 24 for trapping therein, the topsheet 20 is preferably liquid, permeable. In particular, the top sheet may be selected from a variety of textile-like films and fabrics. Suitable fabrics include non-woven materials that are pervious to liquid, soft and pliable. Preferred non-woven materials include spunbonded polypropylene, spunbonded polyethylene, and thermally bonded webs of staple fibers, preferably polypropylene shape or sheath/core bi-component fibers having a core of polyester or polypropylene and a sheath of polyethylene. To enhance the fluid control properties of the aforementioned liners, surfactants or wetting agents typified by X-100 and Triton X-102 available from Rohm & Haas Company of Philadelphia, Pa. may be applied to the fluid receiving zones of the liner selectively having the outer zones untreated to reduce migration of excreted fluid such as urine into the outer absorbent article 10 regions leading to leakage.

If desired, the topsheet 20 may be formed of a liquid impermeable material having plural apertures or pores extending therethrough so as to make the material liquid permeable.

The absorbent core 24 is a rectangular member which is centered in the disposable article 10 and extends from close to the edge of the front portion of the main chassis 14 to close to the edge of the rear portion of the main chassis 16. The absorbent core 24 can be made up of any suitable absorbent material, as well as combinations of different types of absorbent materials. For example, the absorbent core 24 may be formed of a mixture of pulp fluff and SAP wrapped in a liquid permeable tissue wrap. Examples of SAP include polyacrylamides, polyvinyl alcohol, polyacrylates, various grafted starches, and the like. A desired super absorbent material is a cross-linked polysodium acrylate, which can be purchased from BASF Corporation of Portsmouth, Va., under the trademark ASAP 2260. The super absorbent materials can be in various geometric forms, such as various shaped particles, fibers, foams, and layers. The fluff and SAP are present in a ratio of about 11 grams of SAP to 16 gms of fluff for a size 4 diaper, and have a core density range of about 0.14 to 0.22 grams per cubic centimeter.

Moreover, the absorbent core 24 can be of any shape and can be a single, integral absorbent structure, or can comprise a plurality of individual separate absorbent structures and/or absorbent materials that are operably assembled together. It can also consist of air-laid non-woven web that contains super-absorbent particles and/or super-absorbent fibers, polymeric binder and cellulose pulp fibers. In one exemplary embodiment, the absorbent core is sandwiched between two plies of tissue, is aligned on top of the backsheet and adhered down with construction adhesive. The tissue has a basis weight of 17 gsm. Suitable tissues are available from Cellu Tissue Corporation, East Hartford, Conn. The absorbent core 24 is centered along the transverse direction of the absorbent article 10 and registered in the machine (longitudinal) direction within the chassis 12.

The amount of each absorbent material and SAP/fluff ratio depends on the size of the article, e.g., "Small", "Medium", "Large" or "Extra Large."

The disposable absorbent article 10 may also include a pair of conventional "standing leg gathers" or cuffs (not shown) or liquid-impervious gaskets to provide leakage control in the crotch region. The standing leg gathers are located so that they extend along the leg opening region of the diaper as disclosed in U.S. Pat. No. 4,695,278 (Lawson) and U.S. Pat. No. 4,795,454 (Dragoo), both of which are incorporated by reference herein. Each standing leg gather is elasticized and extends along the side marginal edges of the disposable absorbent article 10.

The disposable absorbent article 10 is arranged to be held in place on the body of the wearer in a conventional manner, e.g., by means of a pair of fastening tabs or tapes 50 projecting outward from the pair the ears 26 of the absorbent article 10. In particular, each tape 50 may include a patch of a myriad of small hooks on its underside surface. Each patch is arranged to be releasably secured to a "landing zone" portion 52 on the outer cover of the backsheet 22. The landing zone 52 is located at a position so that when the diaper is folded in half with the front waist portion disposed opposite the back waist portion, the landing zone 52 will be aligned with each tape 50.

The landing zone 52 may comprise a rectangular panel whose outer surface comprises a myriad of small loops arranged to be engaged by the small hooks of the each fastening tape 50.

When the disposable absorbent article 10 is in place on the person with the front portion of the main chassis 14 disposed over the lower abdomen, the rear portion of the main chassis 16 disposed over the lower back and buttocks region, and the crotch portion 18 between the legs, each tape 50 may be brought into engagement with a portion of the landing zone 52 closest to that tape 50 so that the myriad of hooks on the patch engage the myriad of loops of the landing zone 52 to releasably secure the tab thereto. Any suitable multi-hook and multi-loop materials may be used. Particularly suitable multi-hook patches 54 are available from YKK (U.S.A.), Inc., Marietta, Ga., under the model designation Microhook (D-7) or Macrohook (EL "B"), while a particularly suitable multiloop material is a polyester fiber material having a basis weight of 1.55 ounce per square yard with a laminated polypropylene film (8 mil.) backing, available from FAB Industries, Inc., New York, N.Y.

Alternatively the tabs 54 may be in the form of adhesive tapes, such as those available from 3M Corporation, St. Paul, Minn., and the landing zone may be formed of a polyester film with a pre-applied adhesive in a selected print pattern, such as also available from 3M Corporation, St. Paul, Minn.

In use, the disposable absorbent article 10 is fitted around the body of the being. As the ears 26 adjacent the tape 50 are pulled to secure the tape 50 to the landing zone 52 on the backsheet 22 of the main chassis 14, each ear topsheet 28 and ear backsheet 30 tear at the tearable portion 48 thereby exposing the elastic layer 40. As indicated, preferably, the tearable portion 48 is a series of perforations on each ear topsheet 28 and a series of perforations on each ear backsheet 30 that overlap one another. However, any means to allow for easy separation of the ear topsheet 28 and backsheet 30, as described above, is anticipated. The tearable portion 48 preferably extends from the first connecting edge 36 to the second connecting edge 38. The tearable portion 48 may be located anywhere within the ears 26 so long as it is adjacent the central portion of the elastic layer 40. The tearable portion 48 may be adjacent to the distal edge 34 or the proximal edge 32 of the each ear 26. The tearable portion 48 preferably extends in a straight line from the first connecting edge 36 to the second connecting edge 38. However, it is anticipated that the tearable portion 48 can also run in a curved line.

The elastic layer 40 may extend within the ear topsheet 28 and ear backsheet 30 entirely from its distal edge 34 to its proximal edge 32 and from its first connecting edge 36 to its second connecting edge 38. The layer may alternatively extend only within a limited space within the topsheet 28 and backsheet 30.

Although illustrated and described herein with reference to specific embodiments, the present invention nevertheless is not intended to be limited to the details shown. Rather, various modifications may be made in the details within the scope and range of equivalents of the claims without departing from the spirit of the invention.

What is claimed is:

1. A disposable absorbent article arranged to be worn by a living being to trap and collect loose waste of the being, said article comprising:
   (a) a main chassis configured to be worn between the legs of the being, said chassis having a front portion, a rear portion, and a crotch portion connecting said front portion and said rear portion, said chassis comprising a liquid permeable chassis topsheet, a liquid impermeable chassis backsheet, said topsheet directed toward the being's skin, an absorbent core positioned between said chassis topsheet and said chassis backsheet, and a pair of ears integral to said rear portion of said chassis;
   (b) each said ear comprising an ear topsheet and an ear backsheet, each said ear having a proximal edge, a distal edge, a first connecting edge and a second connecting edge, said first connecting edge and said second connecting edge connecting said distal to said proximal edge, said proximal edge of each of said ear topsheet and backsheet integral to said topsheet and backsheet of said chassis;
   (c) each said ear having an elastic layer sandwiched between at least a portion of said ear topsheet and said ear backsheet, each elastic layer having a first edge and a second edge, said first edge secured to said ear topsheet and said ear backsheet and said second edge secured to said ear topsheet and said ear backsheet, said elastic layer having a central portion not secured to either said ear topsheet or said ear backsheet;
   (d) each said ear topsheet and each said ear backsheet having a tearable portion extending from said first connecting edge to said second connecting edge, each said tearable portion extending along said central portion of said elastic layer; and
   (e) a fastener joined to each of said ears to secure the disposable absorbent article about the being's waist; wherein a portion of each ear may be pulled away from the chassis causing each said ear topsheet and each said ear backsheet to tear at said tearable portion thereby exposing said central portion of said elastic layer.

2. The disposable absorbent article of claim 1, wherein the disposable absorbent article is a diaper.

3. The disposable absorbent article of claim 1, wherein said tearable portion on each said ear topsheet overlap said tearable portion on each said ear backsheet.

4. The disposable absorbent article of claim 1, wherein said tearable portion extending from said first connecting edge to said second connecting edge are at a point adjacent said main chassis.

5. The disposable absorbent article of claim 1, wherein said tearable portion extending from said first connecting edge to said second connecting edge are at a point adjacent said distal edge.

6. The disposable absorbent article of claim 1, wherein each fastener comprises a fastening tape extending between said ear backsheet of each of said ears to a landing zone on said backsheet which is arranged to receive said tape.

7. The disposable absorbent article of claim 1, wherein each said fastener is adhesive tape.

8. The disposable absorbent article of claim 1, wherein said fastener includes use of an adhesive.

9. The disposable absorbent article of claim 6, wherein said fastener uses a hook and loop style fastening system.

10. The disposable absorbent article of claim 1, wherein said first edge is secured to said ear topsheet and said ear backsheet and said second edge is secured to said ear topsheet and said ear backsheet by a construction adhesive.

11. The disposable absorbent article of claim 1, wherein said first edge is secured to said ear topsheet and said ear backsheet and said second edge is secured to said ear topsheet and said ear backsheet using ultrasound.

12. The disposable absorbent article of claim 1, wherein said first edge is secured to said ear topsheet and said ear backsheet and said second edge is secured to said ear topsheet and said ear backsheet using themal-mechanical means.

13. The disposable absorbent article of claim 1, wherein said elastic material extends substantially from said proximal edge to said distal edge, and from said first connecting edge to said second connecting edge.

14. The disposable absorbent article of claim 1, wherein said tearable portion is a plurality of perforations.

15. The disposable absorbent article of claim 14, wherein said plurality of perforations includes a series of spaced perforations in a generally straight line.

16. The disposable absorbent article of claim 1, wherein said topsheet is liquid permeable and said backsheet is liquid impermeable.

* * * * *